(12) United States Patent
Podany

(10) Patent No.: US 7,128,720 B2
(45) Date of Patent: Oct. 31, 2006

(54) ULTRASONIC FINGER PROBE

(75) Inventor: Vaclav O. Podany, New Fairfield, CT (US)

(73) Assignee: Ethicon, Inc., Somerville, NJ (US)

( * ) Notice: Subject to any disclaimer, the term of this patent is extended or adjusted under 35 U.S.C. 154(b) by 175 days.

(21) Appl. No.: 10/609,695

(22) Filed: Jun. 30, 2003

(65) Prior Publication Data

US 2004/0267133 A1 Dec. 30, 2004

(51) Int. Cl.
*A61H 1/00* (2006.01)

(52) U.S. Cl. .......................................................... 601/3

(58) Field of Classification Search ................. 601/2–4; 600/439, 459–471
See application file for complete search history.

(56) References Cited

U.S. PATENT DOCUMENTS

| | | | | |
|---|---|---|---|---|
| 4,545,386 A * | 10/1985 | Hetz et al. .................. | 600/462 |
| 4,744,368 A * | 5/1988 | Young et al. ................ | 600/454 |
| 5,088,500 A * | 2/1992 | Wedel et al. ................ | 600/452 |
| 5,242,440 A * | 9/1993 | Shippert ....................... | 606/30 |
| 5,891,026 A * | 4/1999 | Wang et al. ................. | 600/344 |
| 5,986,446 A * | 11/1999 | Williamson .................. | 324/157 |
| 6,193,709 B1 * | 2/2001 | Miyawaki et al. ............. | 606/1 |
| 6,527,767 B1 * | 3/2003 | Wang et al. ................... | 606/32 |
| 6,849,075 B1 * | 2/2005 | Bertolero et al. ............. | 606/41 |
| 2003/0120268 A1 | 6/2003 | Bertolero et al. | |
| 2004/0116921 A1 | 6/2004 | Sherman et al. | |
| 2004/0225217 A1 * | 11/2004 | Voegele et al. ............. | 600/439 |

* cited by examiner

Primary Examiner—Francis J. Jaworski

(57) ABSTRACT

An ultrasonic finger probe including: a body having an ultrasonic transducer disposed therein, the ultrasonic transducer being operatively connected to an ultrasonic generator; and a securing device for securing the body to one or more fingers of an operator.

15 Claims, 3 Drawing Sheets

ULTRASONIC FINGER PROBE

BACKGROUND OF THE INVENTION

1. Field of the Invention

The present invention relates generally to ultrasonic medical instrumentation, and more particularly, to an ultrasonic probe for attachment to one or more fingers of a person.

2. Prior Art

Ultrasonic instruments are well known in the medical arts. Such instrumentation may be used to make lesions in tissue, but are also used to cut and coagulate tissue and blood, respectively. Typically, ultrasonic instrumentation have an ultrasonic transducer at a working end of the instrument, which is typically separated from a handle or other manipulation means by an elongated shaft.

In certain medical procedures, such as a MAZE procedure, lesions are made on the heart in a specific pattern. Often, the lesions are to be made on tissue that is hard to reach with conventional instrumentation or where visibility is poor. Thus, there is a need in the medical arts for a device and methods for easily manipulating the ultrasonic transducer, for accessing hard to reach areas, and which increase the visibility of surgical sites.

SUMMARY OF THE INVENTION

Therefore it is an object of the present invention to provide ultrasonic devices and methods that overcome the disadvantages of conventional ultrasonic instrumentation and methods known in the art.

Accordingly, an ultrasonic finger probe is provided. The ultrasonic finger probe comprises: a body having an ultrasonic transducer disposed therein, the ultrasonic transducer being operatively connected to an ultrasonic generator; and securing means for securing the body to one or more fingers of an operator.

The ultrasonic generator can be remote from the ultrasonic transducer and operatively connected thereto by wiring. The body can have a surface configured for creating lesions in tissue. Furthermore, the body of the ultrasonic transducer can be an elongated bar and can have a length sufficient to span the joints of the one or more fingers to which it is secured.

The securing means can comprise one or more elastic loops fastened to the body and configured for securing one of the one or more fingers to the body, the one or more elastic loops being fabricated from an elastic material. The elastic material can be selected from a group consisting of an elastomer, a fabric, and a composite elastic/fabric. The one or more elastic loops can comprise two elastic loops and the one or more fingers can comprise one finger.

The securing means can also comprise one or more loops, each of the loops having two free ends, one of the free ends having a hook material and the other of the free ends having a loop material, the free ends being wrapped around the one or more fingers and the hook material being secured to the loop material. The one or more loops can comprise two loops and the one or more fingers can comprise one finger.

Also provided is a method for applying ultrasound energy to tissue. The method comprising: providing an ultrasonic finger probe having a body with an ultrasonic transducer disposed therein, the body having a surface for applying ultrasonic energy to tissue; securing the ultrasonic finger probe to one or more fingers of an operator; applying the surface of the ultrasonic finger probe to the tissue; and generating ultrasonic energy and supplying the same to the ultrasonic transducer.

The applying can comprise applying the ultrasonic finger probe on a surface of the heart. The generating can comprise generating ultrasonic energy and supplying the same to the ultrasonic transducer in an amount sufficient to create lesions at least on the surface of the heart.

The method can further comprise repeating the applying and generating steps to create a plurality of lesions by manipulating the ultrasonic finger probe with the at least one finger secured thereto. The manipulating can comprise joining the plurality of lesions to form a single long lesion.

The method can further comprise stabilizing the heart with fingers of a same hand other than the one or more fingers secured to the ultrasonic finger probe.

Still yet provided is an ultrasonic finger probe. The ultrasonic finger probe comprising: an ultrasonic transducer operatively connected to an ultrasonic generator; and securing means for securing the ultrasonic transducer to one or more fingers of an operator.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of ultrasonic transducers and instrumentation, it has been found particularly useful in the environment of creating lesions, particularly for a MAZE procedure. Therefore, without limiting the applicability of the invention to ultrasonic devices configured for making lesions or the use thereof in MAZE procedures, the invention will be described in such environment. Those skilled in the art will appreciate that the ultrasonic devices of the present invention are also useful in other ways known in the art, such as cutting and coagulation of tissue and blood, respectively, and even imaging of tissue and other anatomy.

Figure 1:
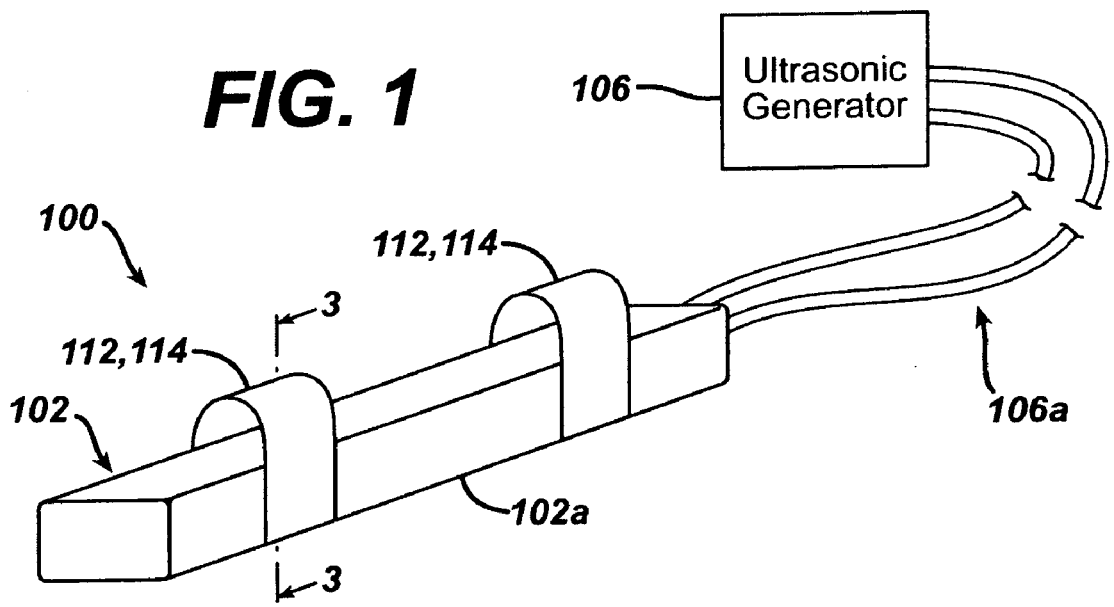
FIG. 1 illustrates an isometric view of an ultrasonic finger probe according to an embodiment of the present invention.
Figure 3A:
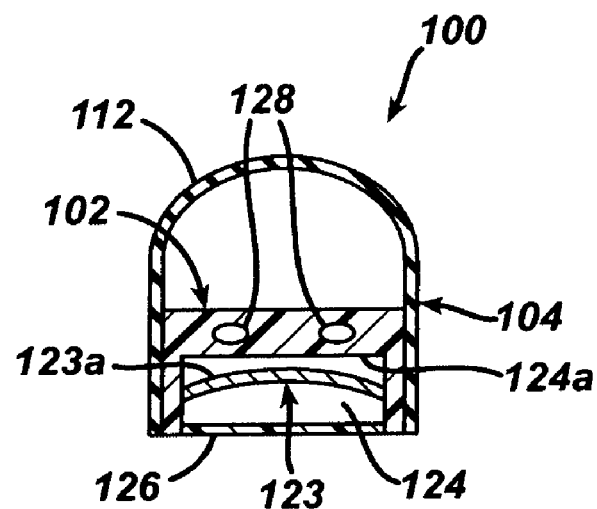
FIG. 3a illustrates a sectional view of a first variation of a securing means as taken along line 3—3 of FIG. 1.
Figure 3B:
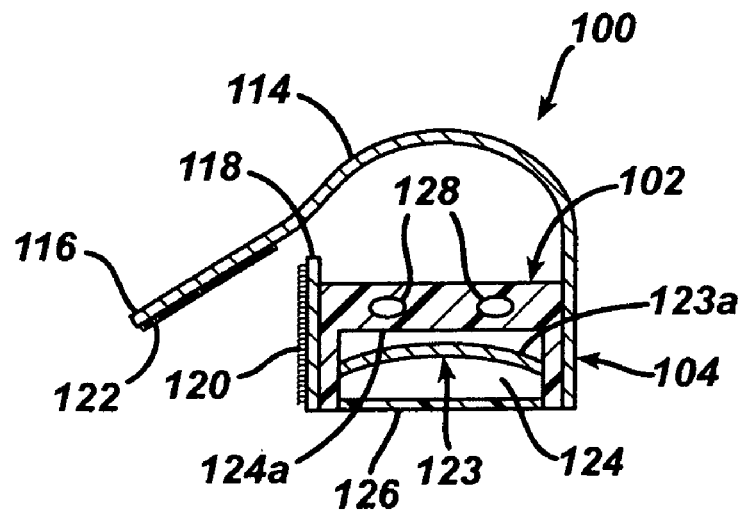
FIG. 3b illustrates a sectional view of a second variation of a securing means as taken along line 3—3 of FIG. 1.

Referring now to FIGS. 1, 3a, and 3b, an ultrasonic finger probe is provided, the finger probe being referred to generally by reference numeral 100. The ultrasonic finger probe 100 has a body 102 which has an ultrasonic transducer 104 disposed therein or thereon (collectively referred to as disposed therein). The ultrasonic transducer 104 is operatively connected to an ultrasonic generator 106. The ultrasonic generator 106 can be integral with the finger probe 100 such as being housed in the body 102 or remotely connected to the ultrasonic transducer 104 by means of wiring 106a or the like. Where the finger probe 100 is used for imaging, the wiring 106a may also return signals to a processor and/or display for display or processing of the ultrasonic imaging corresponding to the signal. The finger probe 100 further has securing means for securing the body 102 to one or more fingers 108 of an operator. Although the finger probe 100 is preferably secured to a single finger 108, those skilled in the art will appreciate that the finger probe 100 can be secured to more than one finger.

The body 102 can have a surface 102a particularly configured for the intended purpose of the finger probe 100, such as for creating lesions in tissue. Thus, the body 102 can be an elongated bar as shown in FIG. 1 with a length sufficient to span the joints 110 of the one or more fingers 108 to which it is secured. The elongated bar 102 and/or the surface 102a can be linear, curved or have linear and curved portions along the length of the body 102. Those skilled in the art will appreciate that different procedures will call for different shaped surfaces 102a to improve the efficacy of the procedure. The body 102 can be fabricated from any materials known in the art for use with ultrasonic transducers, such as thermoplastics or metals.

The securing means can comprise one or more elastic loops 112 as shown in FIG. 3a. Preferably, two such loops 112 are utilized. Each of the elastic loops 112 are fastened to the body 102 and configured for securing the one or more fingers 108 to the body 102. However, the one or more elastic loops 112 do not have to be fastened to the body 102 and could merely be disposed around both the one or more fingers 108 and the body 102. If the finger probe 100 is secured to more than one finger 108, one or more elastic loops 112 can secure each finger 108 to the body 102 or all of the fingers 108 that are secured to the body 102 can share common elastic loops 112. The elastic loops 112 can be fabricated from any resilient material, such as an elastic material. The elastic material can be an elastomer, a fabric, or a composite elastic/fabric. The elastic loops 112 are preferably sized smaller than a typically sized finger and stretch to accommodate the one or more fingers 108 therein. The finger probe 100 can be alternatively connected to one or more fingers of a surgical glove. In yet another alternative, the finger probe 100 can be secured to the one or more fingers 108 by attachment to a glove which itself is secured around the wrist, arm, or hand.

The securing means can alternatively comprise one or more loops 114, as shown in FIG. 3b. Each of the loops 114 has two free ends 116, 118. One of the free ends (118 in FIG. 3b) has a hook material 120 and the other of the free ends (116 in FIG. 3b) has a loop material 122. The hook and loop materials 120, 122 are typically referred to by the trade name Velcro®. At least one of the free ends 116, 118 are wrapped around the one or more fingers 108 and the hook material 120 is secured to the loop material 122.

The body 102 and/or ultrasonic transducer 104 can be configured in any way known in the art for creating lesions, cutting tissue, and/or imaging of tissue, such as that disclosed in co-pending U.S. application Ser. No. 10/609,692, entitled System For Creating Linear Lesions for the Treatment of Atrial Fibrillation, the entire contents of which is incorporated herein by its reference. For example, the ultrasonic transducer can have an ultrasonic crystal 123 housed in a cavity 124 in the body 102 and convexly curved as shown in FIGS. 3a and 3b such that the resulting ultrasonic energy is focused along a straight or curved line along the length of the ultrasonic crystal 123 to create a lesion. The cavity 124 can be covered with an acoustic window 126 fabricated from a suitable material. The ultrasonic crystal 123 may also have an impedance matching coating (not shown) on the side of the ultrasonic crystal 123 that faces the acoustic window 126. The ultrasonic transducer 104 can further provide for circulation of a cooling medium, such as a fluid, through the cavity 124 and/or through one or more conduits 128 provided in the body 102. A cooling medium, for example, water or saline, may be re-circulated through the conduits 128 or through other openings (not shown) in the body 102. The ultrasonic crystal 123 can also be positioned in the cavity 124 such that an air gap exists between a back surface 123a of the ultrasonic crystal and a front surface 124a of the cavity 124. The configuration of the ultrasonic transducer 104 is given by way of example only and not to limit the spirit or scope of the present invention. Those skilled in the art will appreciate that the ultrasonic transducer 104 can be configured in any manner known in the art for producing ultrasonic energy for its intended purpose, whether it be creating lesions in tissue, cutting tissue, or imaging of anatomy proximate the finger probe 100.

Figure 2:
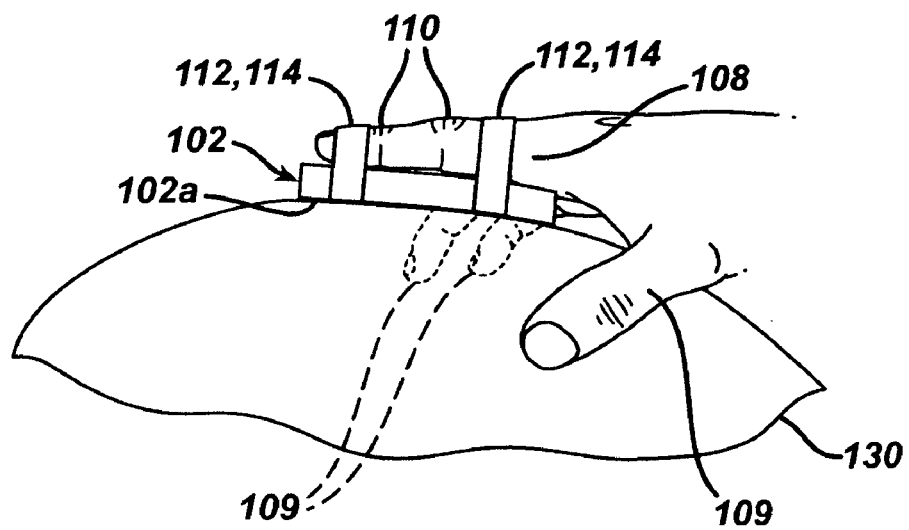
FIG. 2 illustrates the ultrasonic finger probe of FIG. 1 being applied to a surface of the heart and having fingers other then the one(s) secured to the body of the ultrasonic finger probe used to support the heart.
Figure 4A:
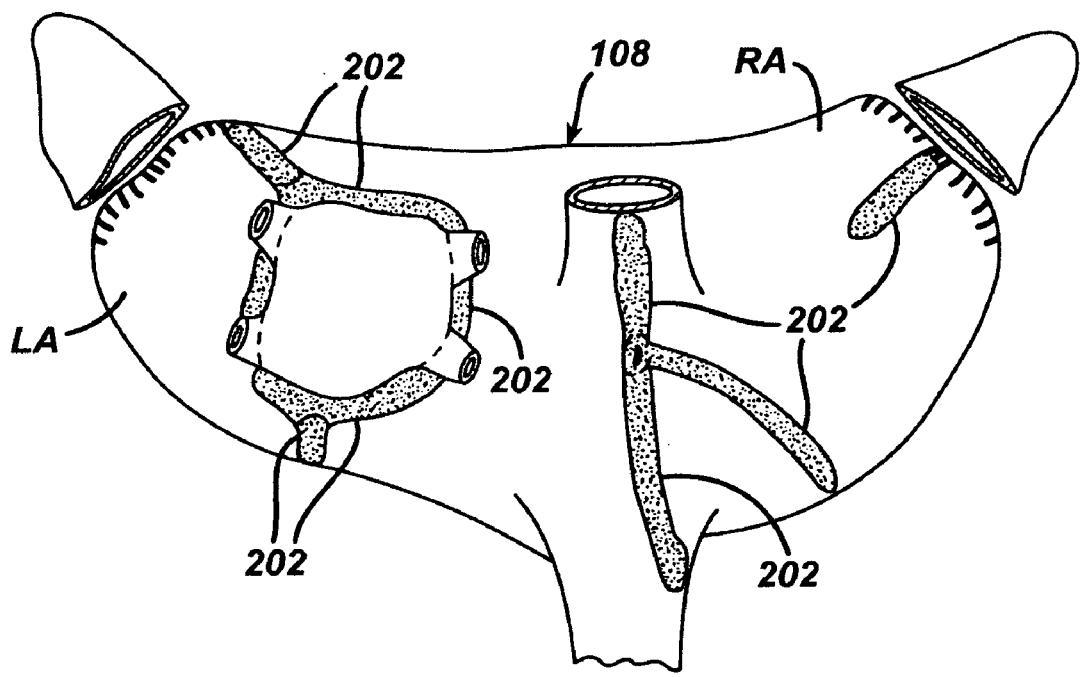
FIGS. 4a and 4b are schematic diagrams of the atria portion of the heart illustrating a pattern of transmural lesions to create a predetermined conduction path in the atrium formed thereon by the ultrasonic finger probe of the present invention.
Figure 4B:
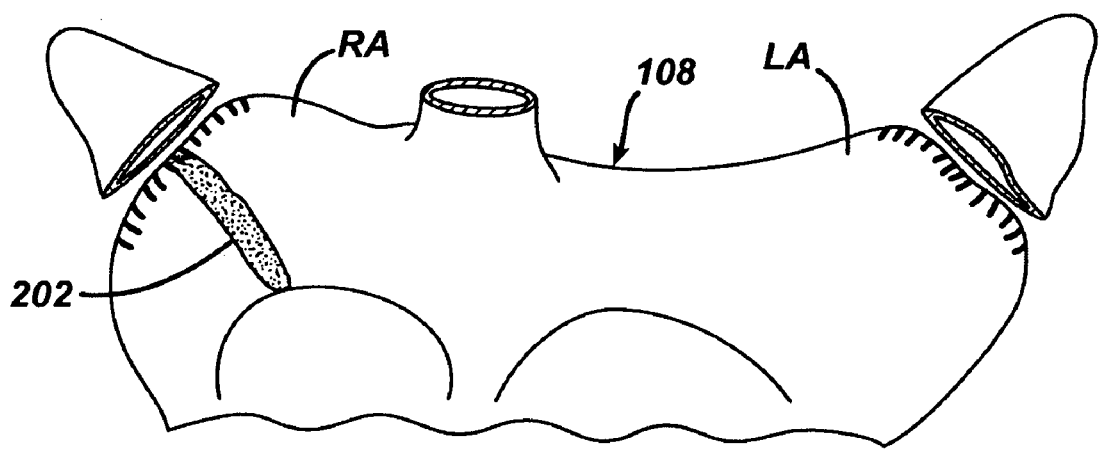

A method for applying ultrasound energy to tissue using the finger probe 100 will now be described with reference to FIGS. 2, 4a and 4b. The method is particularly useful for applying ultrasonic energy to tissue, and more particularly in creating lesions on a surface of the tissue, such as on a surface of the heart. Ideally, the lesions are transmural and created in the heart wall. Firstly, the ultrasonic finger probe 100 is secured to one or more fingers 108 of an operator. As discussed above, the finger probe 100 is preferably secured to a single finger 108, such as the index (pointer) finger 108 and has a length sufficient to span the joints 110 of the finger(s) to which it is secured. Those skilled in the art will appreciate that the finger probe can also be shorter than a length sufficient to span the joints 110 of the finger(s) to which it is attached. In fact, the finger probe can be very small and attached only to a tip of one or more fingers and used to "write" lesions on the heart (i.e., create a continuous lesion line) instead of making linear lesion segments.

The surface 102a of the ultrasonic finger probe 100 is then applied to the tissue and while applied, ultrasonic energy is generated and supplied to the ultrasonic transducer to create lesions. The application of the surface 102a on the tissue can comprise applying the ultrasonic finger probe 100 on a surface of the heart 130. The generation of ultrasonic energy can comprise generating ultrasonic energy and supplying the same to the ultrasonic transducer 104 in an amount sufficient to create lesions at least on the surface of the heart 130 and ideally transmurally in the heart wall. As will be discussed below in an Example, the method can further comprise repeating the applying and generating steps to create a plurality of lesions by manipulating the ultrasonic finger probe 100 with the at least one finger 108 secured thereto. The manipulating can also comprise joining the plurality of lesions to form a single long lesion. As shown in FIG. 2, the heart, or other tissue structure being worked on can be stabilized with fingers 109 of a same hand other than the one or more fingers 108 secured to the ultrasonic finger probe 100. For example, where the finger probe 100 is secured to only the index (pointer) finger 108, the thumb, pinky, ring, and middle fingers 109 can be used to stabilize, hold, and otherwise manipulate the heart 130 (collectively referred to herein as stabilizing).

EXAMPLE

Cardiac arrhythmias, particularly atrial fibrillation, are a pervasive problem in modern society. Although many individuals lead relatively normal lives despite persistent atrial fibrillation, the condition is associated with an increased risk of myocardial ischemia, especially during strenuous activity. Furthermore, persistent atrial fibrillation has been linked to congestive heart failure, stroke, and other thromboembolic events. Thus, atrial fibrillation is a major public health problem.

Normal cardiac rhythm is maintained by a cluster of pacemaker cells, known as the sinoatrial ("SA") node, located within the wall of the right atrium. The SA node undergoes repetitive cycles of membrane depolarization and repolarization, thereby generating a continuous stream of electrical impulses, called "action potentials." These action potentials orchestrate the regular contraction and relaxation of the cardiac muscle cells throughout the heart. Action potentials spread rapidly from cell to cell through both the right and left atria via gap junctions between the cardiac muscle cells. Atrial arrhythmias result when electrical impulses originating from sites other than the SA node are conducted through the atrial cardiac tissue.

In most cases, atrial fibrillation results from perpetually wandering reentrant wavelets, which exhibit no consistent localized region(s) of aberrant conduction. Alternatively, atrial fibrillation may be focal in nature, resulting from rapid and repetitive changes in membrane potential originating from isolated centers, or foci, within the atrial cardiac muscle tissue. These foci exhibit centrifugal patterns of electrical activation, and may act as either a trigger of paroxysmal atrial fibrillation or may even sustain the fibrillation. Recent studies have suggested that focal arrhythmias often originate from a tissue region along the pulmonary veins of the left atrium, and even more particularly in the superior pulmonary veins.

Several surgical approaches have been developed for the treatment of atrial fibrillation. One particular example, known as the "MAZE" procedure, is disclosed by Cox, J. L. et al., *The surgical treatment of atrial fibrillation. I. Summary*, Thoracic and Cardiovascular Surgery 101(3): 402–405(1991) and also by Cox, J. L., *The surgical treatment of atrial fibrillation. IV. Surgical Technique*, Thoracic and Cardiovascular Surgery 101(4): 584–592 (1991). In general, the MAZE procedure is designed to relieve atrial arrhythmia by restoring effective SA node control through a prescribed pattern of lesions about the cardiac tissue wall. Although early clinical studies on the MAZE procedure included surgical incisions in both the right and left atrial chambers, more recent reports suggest that the MAZE procedure may be effective when lesions are created and performed only in the left atrium (see for example Sueda et al., "Simple Left Atrial Procedure for Chronic Atrial Fibrillation Associated With Mitral Valve Disease" (1996)).

The MAZE procedure involves forming lesions in the atrial tissue of the heart 108. In this process, the lesions on the atrial tissue eliminates the atrial arrhythmia by blocking conduction of the aberrant action potentials. FIGS. 4a and 4b show a human heart 108 incorporating a series of strategically positioned transmural lesions 202 throughout the right atrium RA and the left atrium LA formed with the finger probe of the present invention. As shown in FIGS. 4a and 4b, these individual lesions 202 collectively form a pattern of transmurally ablated heart tissue to surgically treat medically refractory atrial fibrillation. The finger probe enables the surgical formation of the series of lesions illustrated in FIGS. 4a and 4b. The process for forming the lesions is more fully described in U.S. Pat. No. 6,161,543, the entire contents of which is incorporated herein by its reference. The lesion shape and pattern is shown by way of example only and not to limit the scope or spirit of the present invention.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An ultrasonic finger probe comprising:
   an elongated body having an ultrasonic transducer disposed therein, the ultrasonic transducer being a crystal operatively connected directly to an ultrasonic generator and having a lesion creating surface, the elongated body having an acoustic window spaced from the crystal and spanning joints of one or more fingers of an operator to which the body is secured; and
   securing means for securing the body directly to the one or more fingers of the operator.

2. The ultrasonic finger probe of claim 1, wherein the ultrasonic generator is remote from the ultrasonic transducer and operatively connected thereto by wiring.

3. The ultrasonic finger probe of claim 1, wherein the body has a surface configured for creating lesions in tissue.

4. The ultrasonic finger probe of claim 1, wherein the securing means comprises one or more elastic loops fastened to the body and configured for securing the one of more fingers to the body, the one or more elastic loops being fabricated from an elastic material.

5. The ultrasonic finger probe of claim 4, wherein the elastic material is selected from a group consisting of an elastomer, a fabric, and a composite elastic/fabric.

6. The ultrasonic finger probe of claim 4, wherein the one or more elastic loops comprises two elastic loops and the one or more fingers comprises one finger.

7. The ultrasonic finger probe of claim 1, wherein the securing means comprises one or more loops, each of the loops having two free ends, one of the free ends having a hook material and the other of the free ends having a loop material, the free ends being wrapped around the one or more fingers and the hook material being secured to the loop material.

8. The ultrasonic finger probe of claim 7, wherein the one or more loops comprises two loops and the one or more fingers comprises one finger.

9. A method for applying ultrasound energy to tissue, the method comprising:
   providing an ultrasonic finger probe having an elongated body with an ultrasonic transducer disposed therein, the ultrasonic transducer being a crystal operatively connected to an ultrasonic generator and the body having a surface for applying ultrasonic energy to tissue including an acoustic window spaced from the crystal and having a length that spans joints of one or more fingers of an operator to which the body is secured;
   securing the ultrasonic finger probe directly to the one or more fingers of the operator;
   applying the surface of the ultrasonic finger probe to the tissue; and generating ultrasonic energy and supplying the same to diagnose and treat the tissue through the ultrasonic transducer.

10. The method of claim 9, wherein the applying comprises applying the ultrasonic finger probe on a surface of the heart.

11. The method of claim 10, wherein the generating comprises generating ultrasonic energy and supplying the same to the ultrasonic transducer in an amount sufficient to create lesions on at least the surface of the heart.

12. The method of claim 11, further comprising repeating the applying and generating steps to create a plurality of lesions by manipulating the ultrasonic finger probe with the at least one finger secured thereto.

13. The method of claim 12, wherein the manipulating comprises joining the plurality of lesions to form a single long lesion.

14. The method of claim 10, further comprising stabilizing the heart with fingers of a same hand other than the one or more fingers secured to the ultrasonic finger probe.

15. An ultrasonic finger probe comprising:

an ultrasonic transducer housed in an elongated body spanning joints of one or more fingers of an operator to which the finger probed is secured, the transducer being a crystal operatively connected to an ultrasonic generator and having a lesion creating surface, and the elongated body having an acoustic window spaced from the crystal; and securing means for securing the ultrasonic transducer directly to the one or more fingers of the operator.

* * * * *